United States Patent [19]

Gibson et al.

[11] Patent Number: 5,527,509
[45] Date of Patent: Jun. 18, 1996

[54] COLORIMETRIC ENZYMIC ANALYSIS

[75] Inventors: Timothy D. Gibson, Rothwell, England; John R. Woodward, Xenia, Ohio; Irving J. Higgins, Wilden, England; William J. Aston, Hailey, England; David A. Griffiths, Sandy, England

[73] Assignee: Cranfield Biotechnology Ltd., Buckinghamshire, England

[21] Appl. No.: 916,117

[22] PCT Filed: Jan. 28, 1991

[86] PCT No.: PCT/GB91/00115

§ 371 Date: Sep. 30, 1992

§ 102(e) Date: Sep. 30, 1992

[87] PCT Pub. No.: WO91/11530

PCT Pub. Date: Aug. 8, 1991

[30] Foreign Application Priority Data

Feb. 1, 1990 [GB] United Kingdom .................. 9002274

[51] Int. Cl.[6] .................................................. G01N 21/00
[52] U.S. Cl. .................................. 422/56; 422/57; 435/10; 435/11; 435/12; 435/14; 435/20; 435/21; 435/25; 435/26; 435/28; 435/805; 435/810
[58] Field of Search ........................ 422/55, 56, 57, 422/58, 59, 60, 82.05; 435/4, 10, 11, 14, 20, 21, 25, 26, 28, 805, 810

[56] References Cited

U.S. PATENT DOCUMENTS

| 4,042,329 | 8/1977 | Hochstrasser | 23/230 B |
|---|---|---|---|
| 4,430,427 | 2/1984 | Hopkins | 435/25 |
| 4,734,360 | 3/1988 | Phillips | 435/25 |
| 4,900,666 | 2/1990 | Phillips | 435/25 |
| 5,200,325 | 4/1993 | Blatt et al. | 435/14 |

FOREIGN PATENT DOCUMENTS

0133481  2/1985  European Pat. Off. .

Primary Examiner—David A. Redding
Attorney, Agent, or Firm—Nikaido, Marmelstein, Murray & Oram

[57] ABSTRACT

A colorimetric enzymic analytical test element comprises a support and a plurality of reaction zones incorporating a dried enzyme composition, dyestuff and reagent adapted to provide a substantial dosage independent colorimetric display when the concentration of an analyte applied to the elements exceeds a predetermined value.

10 Claims, 7 Drawing Sheets

COLORIMETRIC ENZYMIC ANALYSIS

This invention relates to apparatus for colorimetric quantitative enzymic analysis of analytes, particularly but not exclusively those analytes which may be oxidised to directly or indirectly to yield hydrogen peroxide. Preferred aspects of the invention also relate to colorimetric enzymic analytical test strips which are substantially dosage independent, that is the accuracy of the apparatus does not depend on application of a precise quantity of a liquid in which the analyte is present.

The use of enzyme systems to detect and obtain quantitative measurement of analyte concentrations is well established. Various enzyme systems have been stabilised and incorporated into dry reagent formats with the necessary co-factors, colour reagents, buffers etc, needed to produce a compact, accurate and disposable analytical element. Examples include: the Reflotron system; BCL Catalogue; Boehringer Mannheim Technical Data; the Ektachem System of Kodak-Eastman (U.S. Pat. No. 3992158 and EP 0013156); the simple Clinistix or Dextrostix for glucose estimation (Ames Corporation), and many others, Analytes which have been measured include ethanol (EP 0110173 (1983)); creatinine and triglyceride, (Clin Chem 24, 1343 (1978)); cholesterol (EP-A-02562 (1981); uric acid (U.S. Pat. No. 3983005); alanine aminotransferase (DE-32067231 (1982)) and amylase (Clin Chem 24, 1343 (1978)), Subsequent techniques have allowed incorporation of immunological reactions into dry chemistry systems, expanding the analytical technique to include substrates for which direct enzyme determination was not possible. Examples include gentamycin, thyroxine and thyophylline (Clin Chem 30, 194 (1984)) and (EP 0066648 (1987)).

A digital threshold colour control system has been disclosed whereby oxidoreductases utilising NAD(P) as co-factor react on the addition of substrate (the analyte being measured) producing the corresponding product and NAD(P)H (EP 0279988 (1987)). The NAD(P)H was detected by reaction with a tetrazolium salt, using the enzyme diaphorase to mediate colour development. The colour control system utilised the capability of diaphorase, to oxidise NAD(P)H. In the presence of a competing substrate, e.g. benzoquinone, no colour was formed until all the benzoquinone had been reduced. In the presence of excess NAD(P)H the enzyme accepted the tetrazolium salt as a substrate. This reaction may be set to produce colour at a range of levels of the analyte by varying the quantity of competing substrate.

This method has disadvantages. The enzymes utilised require the incorporation of an expensive co-factor. Dehydrogenase enzymes are relatively unstable in the dry state. The number of dye systems that may be used are limited and thus the range of detectable colours is small. Also, colour intensity tends to be low, thus lowering the sensitivity of such systems.

According to a first aspect of the present invention colorimetric enzyme analytical apparatus comprises a test element including a support, the support carrying a zone including a dried enzyme composition, a predetermined amount of a thiol mediator and a dyestuff, the enzyme composition being arranged to produce hydrogen peroxide upon contact of the zone with an analyte, the dyestuff providing a colorimetric display upon reaction with hydrogen peroxide, said colorimetric display being reversible in the presence of the mediator, the mediator being adapted until exhausted to scavenge hydrogen peroxide and prevent said colorimetric display.

A test element may comprise a test strip or alternative configuration known to those skilled in the art. The term "test strip" will be used below for convenience.

A plurality of zones may be provided on a single strip.

The present invention affords advantages which were not previously attainable. A sharp and clearly visible end point dependent on the concentration of an analyte is very beneficial. Although test strips are known which indicate the presence of more than a minimum quantity of an analyte, simple quantitative strips have been elusive. Complex mechanical arrangements have been proposed. The present invention facilitates simple production of dosage independent strips. Arrangements wherein a measured quantity of liquid must be applied are inconvenient and prone to error.

In preferred apparatus in accordance with this invention the display is substantially independent of the amount of liquid applied to the support. Sufficient liquid should be applied to saturate the reagent containing zones but any further liquid present in preferred embodiments of the invention is prevented from penetrating these zones.

In preferred aspects of the present invention a plurality of zones is arranged to provide a display of a respective plurality of incremental values of the analyte concentration. For example end points equivalent to a number of alcohol concentrations may be displayed so that the number of zones in which the colorimetric display is visible can provide a user with a quantitative assessment of the blood or saliva alcohol concentration.

The zones are preferably disposed in spaced relation along the strip. The zones may be arranged to provide similar colorimetric displays upon reaching their respective end points. Alternatively selection of appropriate dyestuffs may allow different colours to be displayed, for example to indicate whether the analyte concentration is above or below a proselected threshold. Selection of suitably reactive combinations of dyestuffs and thiols gives the reversible reaction which may enhance the clarity of the end point. Suitable dyestuffs include combinations of 4-amino antipyrine coupled with substituted phenols, substituted anilines; diamino-substituted aromatics; N,N-disubstituted phenylenediamines coupled with the aforesaid phenols, anilines and aromatics or aminosubstituted heterocycles including pyrazolones and pyrimidines; substituted pyrimidines coupled with the aforementioned couplers; tetramethyl benzidine; substituted naphth-1-ols; 9-ethylcarbazole and others known to those skilled in the art.

The term "dyestuff" used in this specification refers to compounds which may change colour or become coloured in the presence of hydrogen peroxide or other intermediate. Redox dyes or materials which condense to form dyes may be provided.

Preferred embodiments of the invention incorporate a peroxidase adapted to catalyse the reaction of the dyestuff and hydrogen peroxide.

Although a large number of mediators may be employed in quantitative enzymic assay systems, for example as proposed in U.S. Pat. No. 4042329 (Hochstrasser), the majority are not commercially acceptable. We have found that selection of thiols from the wide range of possible reducing agents is particularly advantageous.

The mediator which serves as a peroxide scavenger may be selected from the many thiols available.

Preferred mediators include thiol sulphonates for example sodium mercaptoalkyl sulphonates including sodium mepcaptoethane sulphonate and sodium mepcaptopropane sulphonate; dithioepythritol, dithiothreithol and thioglycollic acid sodium salt, although the latter compound is air sensitive and has an unpleasant stench. Polymepic mediators having thiol groups such as thiolated dextran, for example mepcaptodextran may also be used. In addition to efficient reaction with hydrogen peroxide, preferred mediators ape soluble in water and are stable both on storage and during use. Prolonged oxidative stability in solution is not important. Colour enhancers, mordants and inhibitors may be added to modify and enhance the colour reaction. Promotors, cofactors and the like may also be employed.

Enzyme compositions which may be used include single oxidases of mixtures thereof. These may be conjugated to immunologically active molecules so as to allow immunological determinations. The compositions may include promotors or co-enzymes and also may incorporate compounds introduced to stabilise the enzymes in the dry state. The enzyme composition may produce hydrogen peroxide directly by reaction with the analyte. Alternatively the composition may produce hydrogen peroxide indirectly by conversion of the product of the enzyme reaction.

The zones of preferred apparatus may be provided with a microporous overlay. This serves to isolate the reagents from the body of liquid applied to the test strip. Solid particles, such as blood cells which may interfere with the colorimetric display, are isolated from the reagents. The absorbancy of the underlying matrix is limited by the overlay affording substantial dosage independence. The rate of enzymic reaction is enhanced. This unexpected result is very advantageous since the colorimetric display is developed more rapidly. This is particularly important for test strip applications. This effect may be attributable to localised elevated oxygen concentrations caused by the small volume of liquid in the reagent zone.

The microporous overlay may be selected from any suitable material, including ethyl cellulose, cellulose acetate and substituted cellulose derivatives. The overlay may be cast from organic phase solution onto the surface of the test strip.

A membrane may be arranged to cover the enzyme containing zone. This may serve to limit the volume of liquid available to the enzyme containing zone, affording virtually complete dosage independence. The membrane may also incorporate a separation facility to screen blood cells and other particles from the reagents. Reactions for additional reaction stages may be disposed above the membrane, for example for precipitation of low density lipoproteins for a high density lipoprotein determination. Preliminary enzyme reactions e.g. lipase catalysed reactions, may be carried out in a layer disposed above the membrane. This may overcome the reluctance of hydrophobic compounds to penetrate hydrophilic membranes.

Analytes to which the present invention is applicable include alcohol, cholesterol, lactate, uric acid, glycerol, triglycerides, glutamate, glucose, choline, NADH and many others. The enzyme composition may be selected from alcohol oxidase (especially from Hansenula polymorpha because this enzyme has good stability in use, affording beneficial storage properties) cholesterol oxidase, NADH oxidase (to allow dehydrogenases to be used), selected in accordance with the analyte to be detected. Ethanol may be determined using alcohol oxidase and horseradish peroxidase. Alternative peroxidases include lactoperoxidase and microperoxidase.

The present invention may also produce a method of colorimetric enzymic analysis comprising use of the apparatus as previously disclosed. The reagents may be applied to the support by printing, for example screen printing and mask printing. This facilitates commerical production of test strips or other apparatus in accordance with this invention.

The method may further comprise application of a microporous coating or overlay to the enzyme composition and other reagents. A membrane may be subsequently or alternatively applied.

In preferred methods of analysis a quantity of liquid containing the analyte is deposited on the support, preferably upon the overlay or any superimposed membrane or reaction pad and allowed to contact the reagent composition after passage through any such membrane or pad. When the composition has been saturated with the liquid, the membrane may be removed or wiped clean to allow inspection of the colorimetric display.

In preferred embodiments of the invention the enzymes are stabilised in accordance with the disclosure of PCT/GB89/01346. This specification discloses protection of enzymes against denaturation upon drying by mixture with aqueous solutions of cationic polyelectrolytes and cyclic polyols. Mixtures of lactitol, sorbitol, inositol, lactose, maltose or sucrose can be used in conjuction with DEAE-dextran or analogous charged polymers.

The amount of polyol may lie in a preferred range of 1 to 20%, more preferably 2 to 10%, most preferably 5 to 10%. The polyelectrolyte, preferably DEAE-dextran or chitosan may have MW of 5000 to 500000, preferably 5000 to 20000, more preferably 5000 to 10000. An amount of 0.1 to 10% especially 0.5 to 2% is preferred. The pH at which the enzymes are dried is important and should be optimised by simple experimentation. For example alcohol oxidase may be dried at pH 7.8, although cholesterol oxidase may be dried at pH 5 or 9.

Anionic polyelectrolytes may be used in place of cationic polyelectrolytes dependent on the enzyme concerned. For example peroxidase or alcohol oxidase may be stabilised in accordance with the disclosure of GB 9006642.4.

Preferred apparatus in accordance with this invention comprises a test strip carrying one or a plurality of zones or regions containing the enzyme mediator and dyestuff compositions. The backing is preferably impermeable and supports one or more portions of carrier material, each portion defining a said zone or region. The analytical zones may be surrounded by absorbant material arranged to absorb excess analyte liquid applied to the surface of the test strip. The carrier material may be secured to the backing by any convenient means. Adhesives which may be employed preferably contain no biochemically active or inhibitory ingredients which can interfere with the, operation of the enzyme compounds. A solution of a polymer from which the backing strip is formed in an appropriate solvent may be used. Thus a polyolefin backing strip may have the analytical regions secured to it by softening the backing strip using trichloroethane or other appropriate solvent.

In preferred embodiments of the invention a plurality of analytical zones or regions may .each incorporate a different amount of a mediator and thereby be arranged to detect a corresponding predetermined amount of the analyte. Thus ethanol at concentrations of 300, 500 and 800 mg $l^{-1}$ may be detected on respective regions of the test strip. The dyes for each region may be the same or different. Thus differently coloured dyes may be arranged to indicate different analyte concentrations.

BRIEF DESCRIPTION OF THE DRAWINGS

This invention is further described by means of examples but not in any limitative sense, with reference to the accompanying drawings of which.

The following experimental techniques were employed.

1) Enzymes

Alcohol oxidase (EC 1.1.3.13), isolated and purified from a methylotrophic yeast (*Hansenula polymorpha*) was added to give a concentration of 100–300 units $cm^{-3}$, preferably at 200 units $cm^{-3}$ Peroxidase (EC 1.11.1.7), isolated and purified from horseradish, (Sigman Type II) was used in a concentration 10–200 units $cm^{-3}$, preferably at 100 units $cm^{-3}$. Lactoperoxidase or microperoxidase may also be used.

2) Stabilisers

These were added primarily to stabilise the enzymes, especially alcohol oxidase (EC 1.1.3.1.3). The stabilisers were added to a final concentration of 50 mg $cm^{-3}$ in the case of inositol and dextran. The combination of lactitol and diethylaminoethyldextran (DEAE-Dextran) were added to a final concentration of 50 mg $cm^{-3}$ and 10 mg $cm^{-3}$ respectively.

3) Buffers

Various buffer systems may be used. For example sodium phosphate buffers at pH 7.0 to 8.0 were used the molarity being varied between 20 and 100 mM. 3,(N-morpholino)propane sulphonic acid (MOPS) was a preferred buffer, aiding the reaction and colour development. This was used at pH 7.8–8.0 at 10–100 mM.

4) Detection systems

Peroxide detection systems are many and varied. The non-carcinogenic benzidine derivative 3,3',5,5'-tetramethyl benzidene develops a blue colour upon reaction with peroxide and peroxidase and has been used extensively in dry strip reactions. This was tested and found to be unsuitable as the hydrochloride salt, producing coloured strips in some cases upon drying, or forming no colours at all on development. However the free base overlaid upon the enzymes from an organic phase was acceptable.

Other systems comprising substituted anilines or phenols in conjuction with heterocyclic compounds such as 4-amino antipyrine (4AAP) or 3-methyl-2-benzothiozolinone hydrazone (MBTH) were found to be more stable and produced satisfactory colours when reacted with peroxide in the presence of peroxidase. N,N Disubstituted phenylene diamines, tetrasubstituted pyrimidines, 9-aminoethyl carbazole or 4-substituted-1-naphthols may also be used. The preferred dye systems respond to the mediator reaction employed in the presence of any associated buffer/mordant/additives.

The concentration of any heterocyclic dyestuffs used was held in the range of 10–50 mM.

5) Mediators

Various mediators have been used. These included cysteine, cysteine hydrochloride, sodium mercaptoethyl sulphonate, sodium mercaptopropyl sulphonate, dithiothreitol, dithioerythritol, reduced glutathione, mercaptodextran, thioglycollic acid, thiopyridine, 2-thiouracil, 2-mercaptothiazoline. Further mediators may be employed, e.g. cysteamine, cysteine ethyl or methyl esters, 2-mercaptopyridine. Bisulphites and sulphites which have S-H linkage containing tautomers are also useful and economical but are labile in acid solution.

The preferred mediators were cysteine, cysteine hydrochloride and sodium mercaptoalkyl sulphonates. These were found not to inhibit the enzyme or to be unstable at ambient temperature.

Example 1 Threshold Test for Glucose Filter paper Whatman 3 mM Chromatography Grade was saturated with a series of solutions containing:

| | |
|---|---|
| Glucose oxidase | 200 units |
| Peroxidase | 100 units |
| Inositol | 50 mg |
| 4-Amino antipyrine | 20 mMolar |
| 3-Hydroxy-2,4,6-tribromobenzoic acid | 25 mMolar |
| Bovine serum albumin | 30 mg |
| in 1.0 ml pH 7.9 100 mM MOPS buffer | |

The mediator (cysteine) concentration was varied from 1 mg to 8 mg in 1 mg steps.

Figure 1:
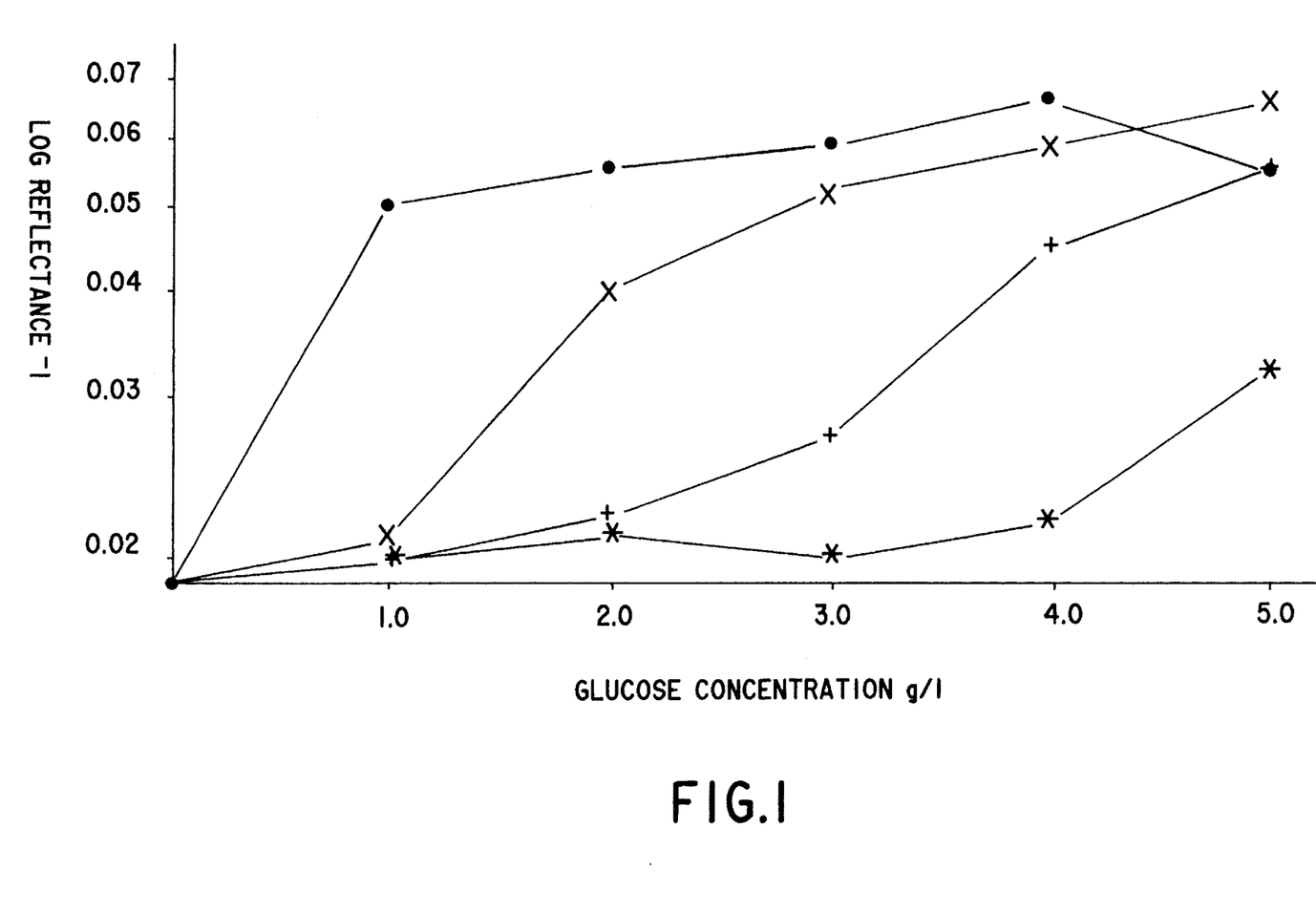
FIGS. 1 to 5 are graphs showing the results of Examples 1 to 5.

The saturated papers were dried for 30 minutes at 30°–35° C. in a vacuum oven and discs (5 mm) were cut from the dried papers and mounted on paper or card by adhesion to plastics solution (solvent: 1,1,1-trichloroethane). Standard glucose solutions were used to develop the discs, 8 μl being the added. The final colour formation was measured using a De Lange microcolour reflectometer. The results shown in Table 1 are expressed graphically in FIG. 1 (●is a plot of 1 mg/ml cysteine; x is a plot of 4 mg/ml cysteine; + is a plot of 6 mg/ml cysteine; and * is a plot of 8 mg/ml cysteine. The horizontal line in the plot indicates the minimum log reflectance at which color appears).

Examples 2 and 5 Threshold Tests for Cholesterol

Filter paper (Watman 3 mm Chromatography Grade) was saturated with a series of solutions containing:

| | |
|---|---|
| Cholesterol oxidase | 50 units |
| Peroxidase | 100 units |
| Lactitiol | 50 mg |
| DEAE dextran | 10 mg |
| 4-Amino antipyrine | 20 mmolar |
| 3-Hydroxy 2,4,6-tribromobenzoic acid | 25 mmolar |
| Sodium cholate | 5 mg |
| in 1.0 ml, pH 7.9, 20 mM MOPS buffer. | |

Figure 2:
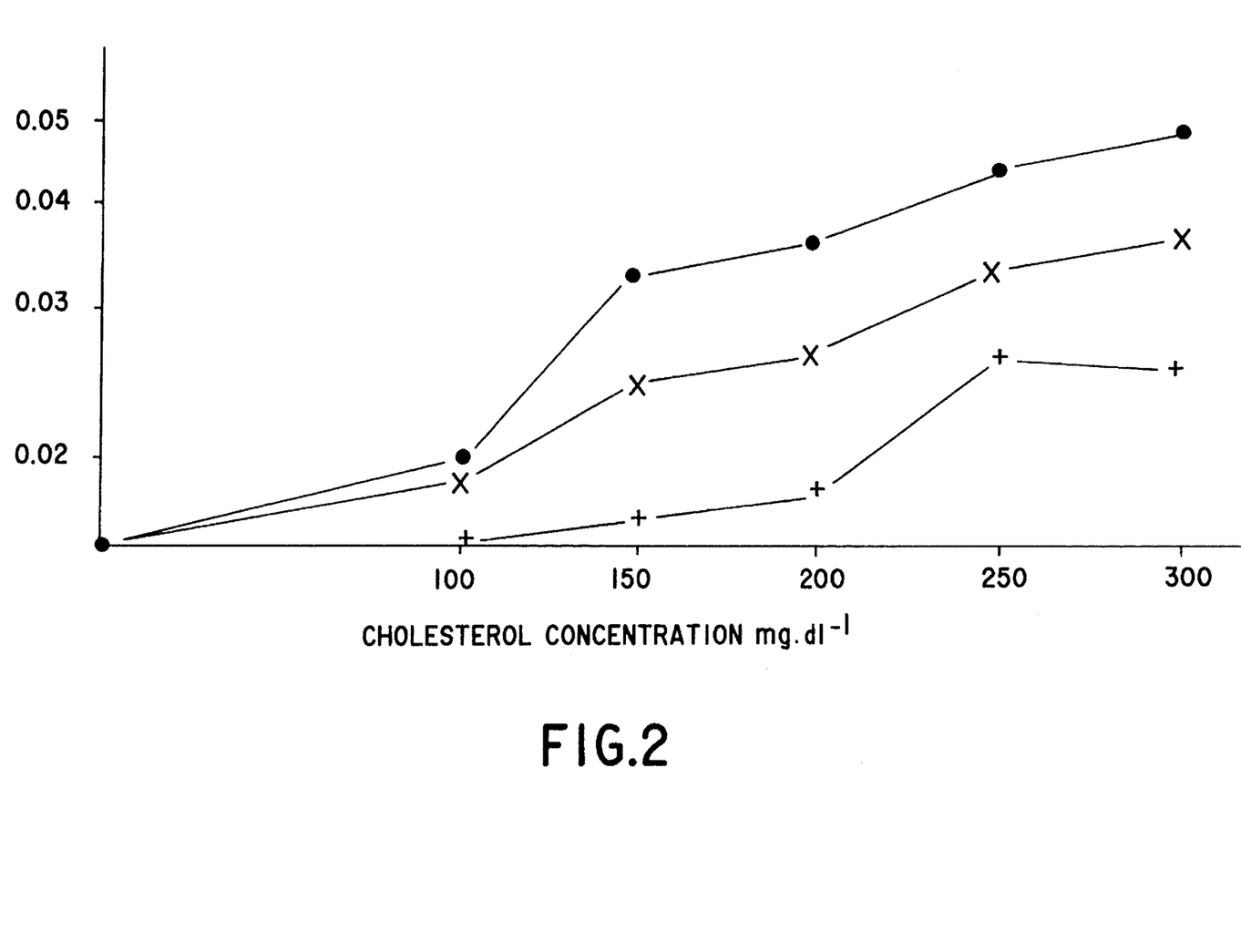
Figure 5:
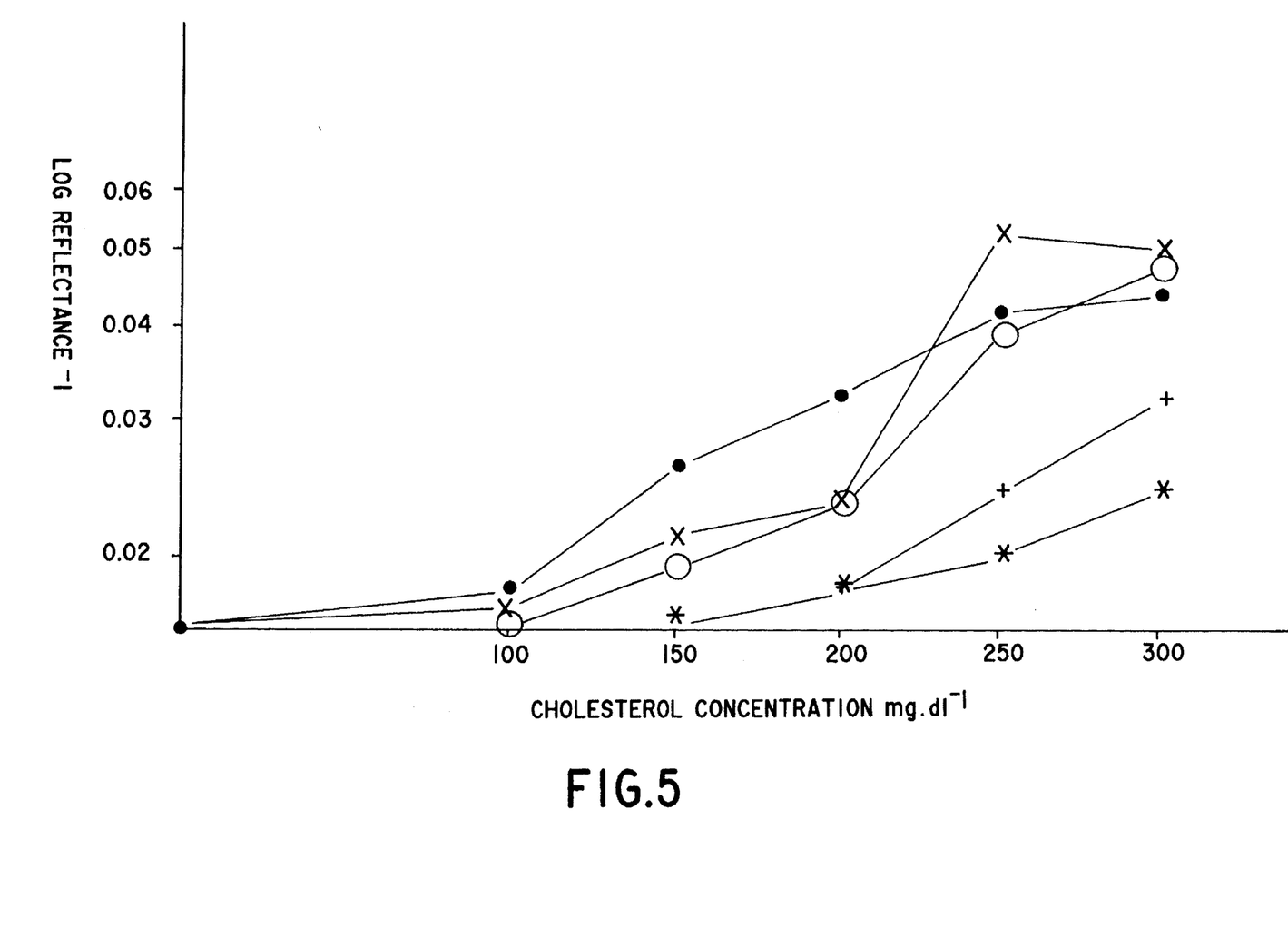

The mediator cysteine (Example 2) or sodium mercaptoethane sulphonate (Example 5) concentrations were varied from 1.0 to 7.0 mg $cm^{-3}$ in the final solution. All subsequent steps were as for Example 1, except that standard cholesterol containing serum samples (Sigma Lipid E) were used to develop the discs. The results are shown in Table 2, FIG. 2 (● is a plot of 1 mg/ml cysteine; x is a plot of 4 mg/ml cysteine; and + is a plot of 6 mg/ml cysteine. The horizontal line in the plot indicates the minimum log reflectance at which color appears); and after "FIG. 5" insert (● is a plot of 2 mg/ml cysteine; x is a plot of 3 mg/ml cysteine; ⊙ is a plot of 4 mg/ml cysteine; + is a plot of 6 mg/ml cysteine; and * is a plot of 7 mg/ml cysteine. The horizontal line in the plot indicates the minimum log reflectance at which color appears) and Table 5, FIG. 5.

Examples 3 and 4 Threshold Tests for Alcohol

Figure 3:
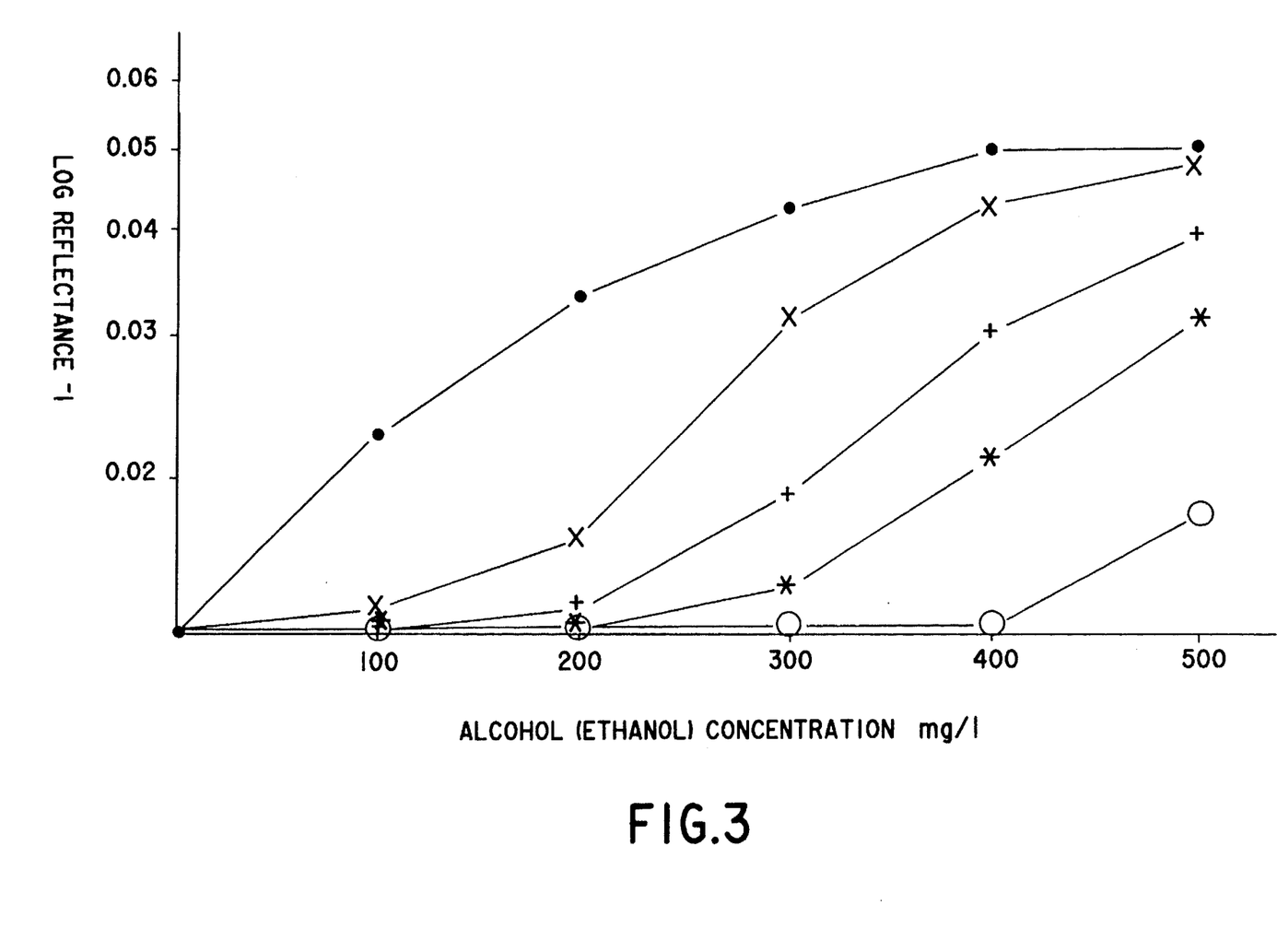
Figure 4:
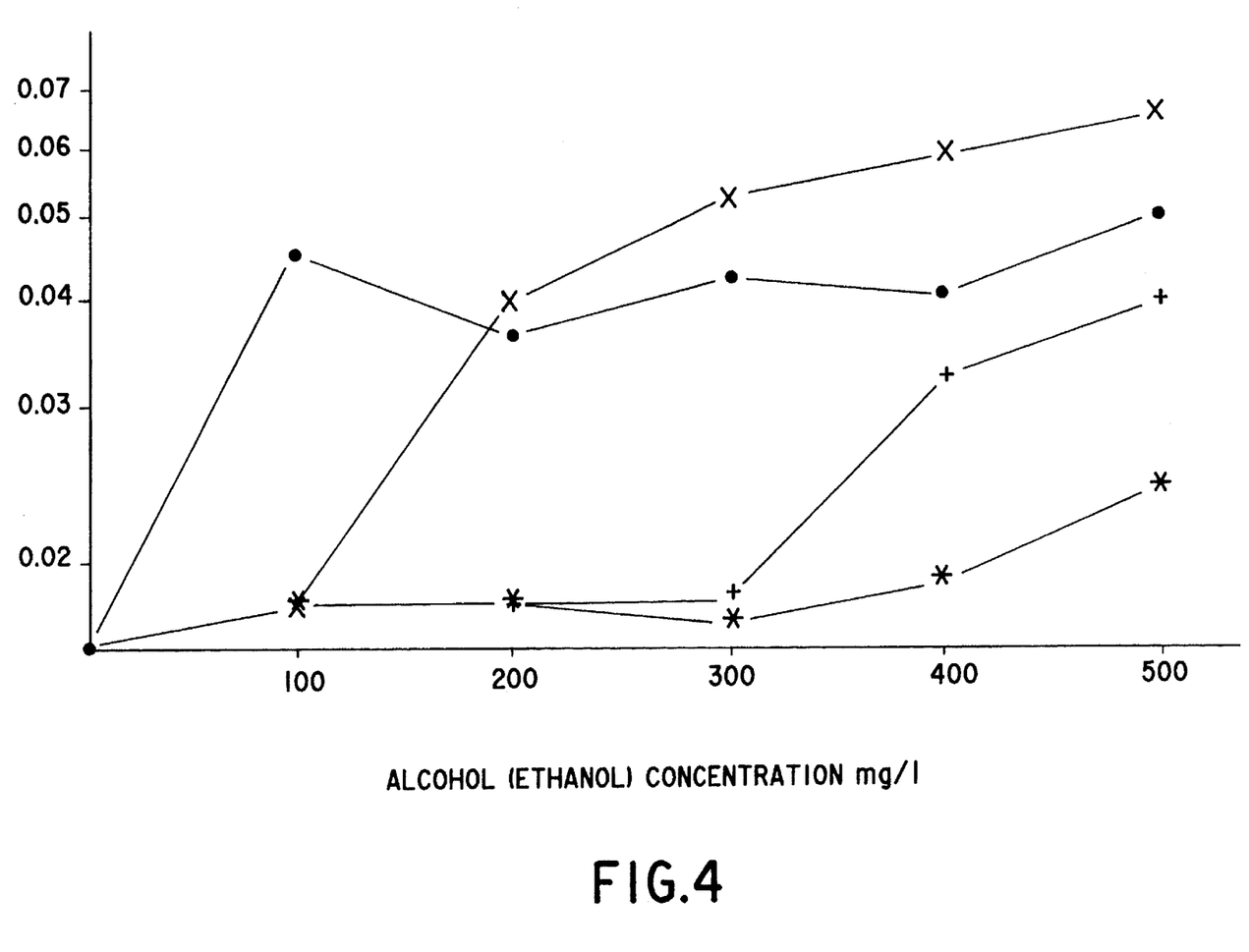

The composition of these tests were exactly as Example 1 except that the glucose oxidase was replaced with alcohol oxidase. Example 3 used 3-hydroxy-2,4,6-tribromobenzoic acid as the dye compound whereas Example 4 used N,N,bis hydroxyethyl 3-toluidine. In both cases the mediator was cysteine at 1 mg to 8 mg cm$^{-3}$ The discs formed were developed using aqueous standard ethanol solutions. The results are shown in Tables 3 and 4 and FIGS. 3 (● is a plot of 1 mg/ml cysteine; x is a plot of 2 mg/ml cysteine; + is a plot of 3 mg/ml cysteine; * is a plot of 4 mg/ml cysteine; and ⊙ is a plot of 5 mg/ml cysteine. The horizontal line in the plot indicates the minimum log reflectance at which color appears); and after "and 4" insert (⊙ is a plot of 1 mg/ml cysteine; x is a plot of 2 mg/ml cysteine; + is a plot of 4 mg/ml cysteine; and * is a plot of 5 mg/ml cysteine. The horizontal line in the plot indicates the minimum log reflectance at which color appears) and 4.

Figure 6:
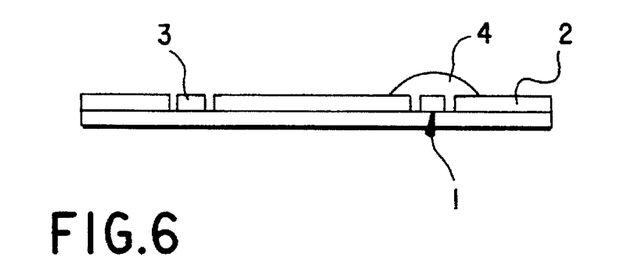
FIG. 6 is a cross sectional view of a test strip in accordance witch this invention.
Figure 7:
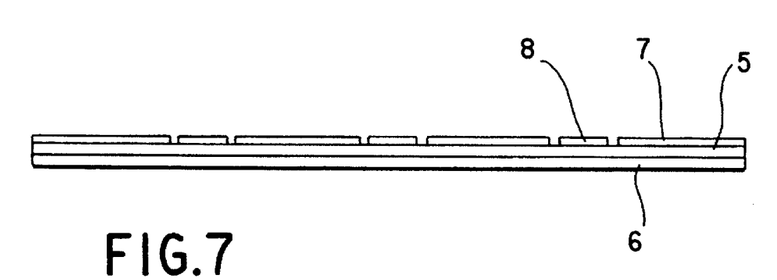
FIG. 7 is a cross sectional view of a further test strip in accordance with this invention.
Figure 8:
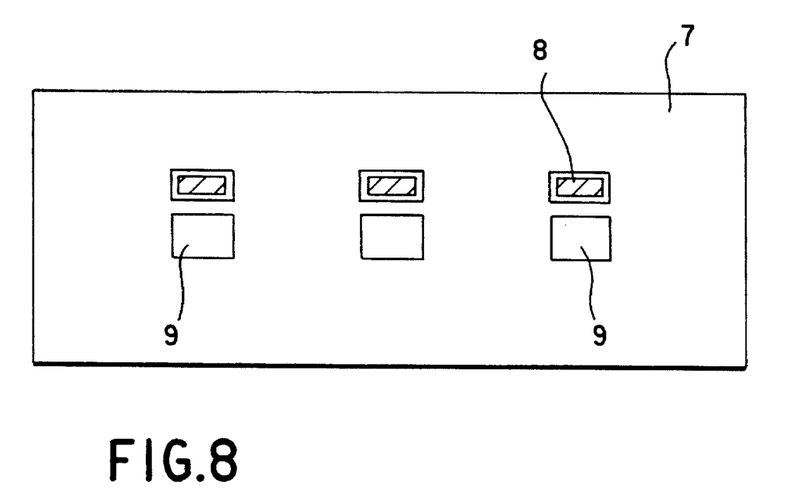
FIG. 8 is a plan view of the test strip shown in FIG. 7.

FIGS. 6 and 7 illustrate construction of test strips in accordance with this invention. The test strip shown in cross section FIG. 6 comprises a non absorbant backing support carrying an absorbant card 2, the card having a plurality of perforations within which enzyme containing discs 3 are disposed, The discs 3 may cylindrical although alternative configurations, which facilitate communication with the surrounding absorbant card, may be employed. The discs 3 are secured to the backing by use of an inert adhesive for example dissolved plastic in trichloroethane. In use of the test strip the body of liquid to be analysed, for example alcohol-containing saliva is deposited on the test strip as shown in FIG. 6. Overlap of the liquid between the enzyme disc 3 and surrounding absorbant card 2 faciliates absorption of the excess liquid into the card to provide a metered application of liquid to the enzyme disc. Hydrogen peroxide generated by oxidation of ethanol in the liquid is scavenged by the mediator until the mediator is exhausted. Any excess ethanol in the liquid sample above the selected threshold or end point produces hydrogen peroxide which is not scavenged and which oxidises the dye producing a colour reaction.

FIG. 7 illustrates an alternative embodiment of the invention wherein an absorbant layer 5 is disposed between two impermeable layer 6, 7. Enzyme containing discs 8 disposed along the strip contain different pre-determined quantities of the mediator and therefore exhibit different end points, for example indicative of alcohol concentrations of 0.3, 0.5 and 0.8 gl$^{-1}$. The sample may be applied remotely directly onto the absorbant layer 9 and thus transferred to the reverse side of the analytical region. This produces a relatively dose independent system. Further this one strip of absorbant layer may contain all analytical elements as shown in FIG. 7. In alternative embodiments of the invention the enzyme containing disc may be overcoated with, for example 1% solution of ethyl cellulose in toluene. Such a coating serves as a filter, for example preventing absorption of red blood cells into the enzyme containing disc. In addition the overcoating reduces the rate of permeation of sample into the disc, metering the liquid into the latter and prevents contact between the enzyme and the body of non-absorbed liquid.

Figure 9:
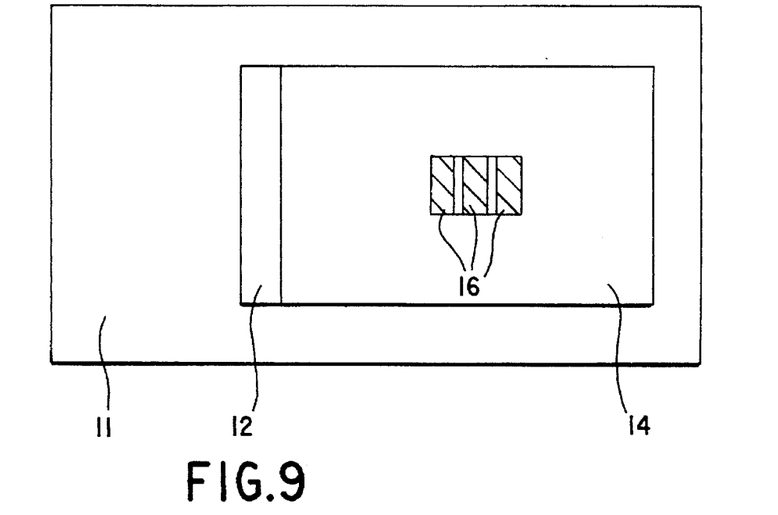
FIG. 9 is a plan view of appratus in accordance with this invention.
Figure 10:
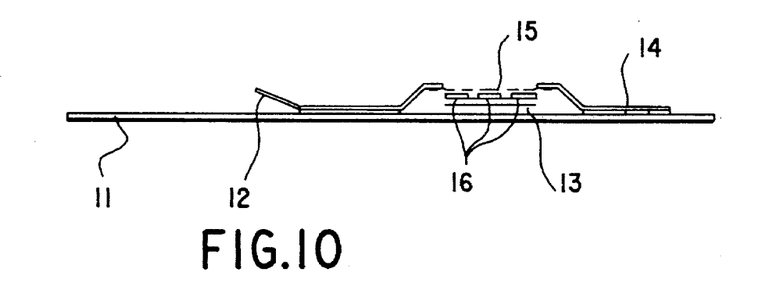
FIG. 10 is a cross section through the apparatus of FIG. 9.

FIGS. 9 and 10 illustrate alternative apparatus in accordance with the invention. Three reagent zones 16 are secured to a backing card 11 by means of an adhesive strip 13. The three zones 16 each incorporate a dried enzyme composition, dyestuff and different levels of the mediator to provide three different preselected end points. A Nucleopore, Isopore, Cyclopore, Nylon, PTFE, Polyester or other suitable membrane 16 overlies the zone 16 and is secured to the backing card by means of a waterproof peel-off strip 14 having a tab 12 to facilitate manual removal. In use of the apparatus a quantity of liquid containing the analyte, for example saliva or blood is applied to the membrane 15 and allowed to penetrate to the zone 16. The tab 12 may then be pulled to remove the peel-off strip 14 so that the colorimetric display may be observed.

Figure 11:
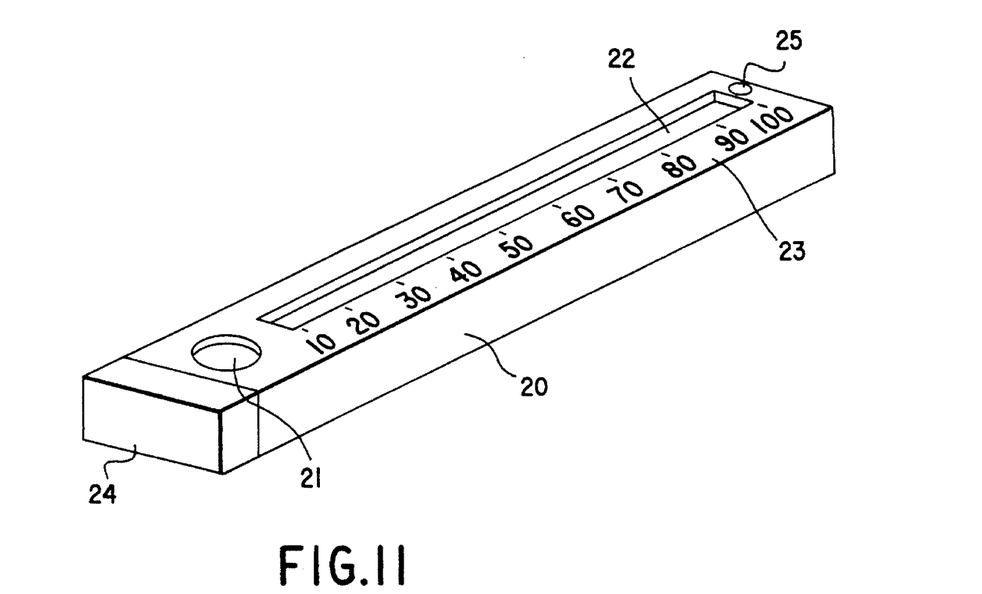
FIG. 11 shows a further apparatus in accordance with the invention.

FIG. 11 illustrates alternative apparatus in accordance with this invention. An elongate carrier 20 includes a linear test strip 22 impregnated with a dried stabilised enzyme composition which may be immobilised, immobilised dyestuff and immobilised thiol mediator. An absorbant pad 21 is arranged to receive a quantity of liquid to be analysed. A reservoir 24 contains a buffer solution adapted to cause the analyte containing liquid to diffuse along the strip 22. A reservoir 24 may be provided with a seal which can be ruptured to release the buffer in use. Passage of the analyte containing liquid along the strip 22 creates a colorimetric display by oxidation of the dyestuff when the thiol mediator has been consumed. The distance to which the colorimetric display passes along the strip in relation to a graduated scale 23 affords an indication of the concentration of analyte within the liquid applied to the receptacle 21. Use of a mediator provides an analyte threshold below which a response is not observed, avoiding a need to have a zero point on the scale 23. This allows use of a shorter strip economising on materials and giving more rapid rsponse. The scale may be arranged to provide a display only when the analyte concentration exceeds a predetermined value, for example the legal blood alcohol limit for drivers. Full development of the test strip is revealed by a control spot 25 at the end of the strip 22 remote from the receptacle 21.

In an alternative embodiment of this invention, enzyme labelled immunologically active compounds (antibodies) may be quantitated using the appropriate mediated system. Immunologically active compounds (antibodies) which may be free or immobilised may be used to specifically recognise and complex molecules (analytes) in a sample. Reaction of the enzyme-labelled immunologically active compound (antibody) with said analyte or analyte-complex enables a quantifiable detection reaction to take place. Incorporation of specific mediator concentrations into the detection reaction allows semi-quantitation of the analyte complexed in the immunological reaction, e.g.

| | | |
|---|---|---|
| 1. Immunological + Antibody | Analyte ---> | Immobilised Antibody Analyte Complex |
| 2. Immobilised + Antibody Analyte Complex | Enzyme labelled ---> Antibody | Immobilised Antibody Analyte Enzyme Labelled Antibody Complex |

| 3. Immobilised + Antibody Analyte Enzyme Labelled Antibody Complex | Enzyme ---> Substrate | Enzyme Product |
|---|---|---|
| | Mediator ---> | No Colour Mediator ---> Exhausted |  Colour |

Preferred examples are:

1. Enzyme Label:Alkaline Phosphatase

Enzyme Substrate:Glucose 6-Phosphate

Enzyme Products:Glucose+Phosphate

Mediator Reaction:Glucose Oxidase/Peroxidase

2. Enzyme label:Alkaline Phosphate

Enzyme Substrate:Glyceraldehyde 3-Phosphate

Enzyme Product:Glyeraldehyde+Phosphate

Mediator Reaction:Glyceraldehyde 3-Phosphate Oxidase/Peroxide

3. Enzyme label:beta-D-Galactosidase

Enzyme substrate:Lactose

Enzyme Product:Galactose and Glucose

Mediator Reaction:Glucose Oxidase/Peroxide

TABLE 1

Threshold Test for Glucose

| Glucose Concentration | Reflectance$^{-1}$* Mediator (Cysteine) mgml$^{-1}$ | | | |
|---|---|---|---|---|
| gl$^{-1}$ | 1.0 | 4.0 | 6.0 | 8.0 |
| 1.0 | 0.050 | 0.021 | 0.020 | 0.020 |
| 2.0 | 0.056 | 0.040 | 0.022 | 0.021 |
| 3.0 | 0.059 | 0.053 | 0.027 | 0.020 |
| 4.0 | 0.067 | 0.059 | 0.027 | 0.022 |
| 5.0 | 0.056 | 0.063 | 0.056 | 0.033 |

Reflectance$^{-1}$ Blank disc (developed with H$_2$O) 0.019
*A reflectance$^{-1}$ value of 0.022 or below indicates no visible colour formation.

TABLE 2

Threshold Test for Cholesterol
Dye: 3-Hydroxy 2,4,6 Trimbromobenzoic Acid

| Cholesterol Concentration | Reflectance$^{-1}$* Mediator (Cysteine) mgml$^{-1}$ | | |
|---|---|---|---|
| gl$^{-1}$ | 1.0 | 4.0 | 6.0 |
| 100 | 0.020 | 0.019 | 0.016 |
| 150 | 0.032 | 0.024 | 0.017 |
| 200 | 0.035 | 0.026 | 0.018 |
| 250 | 0.043 | 0.033 | 0.026 |
| 300 | 0.048 | 0.036 | 0.025 |

Reflectance$^{-1}$ of a blank disc 0.016
*A reflectance$^{-1}$ value of 0.019 or below indicates no visible colour formation.

TABLE 3

Threshold Test for Alcohol.
Dye: 3-Hydroxy 2,4,6 Trimbromobenzoic Acid

| Alcohol Concentration | Reflectance$^{-1}$* Mediator (Cysteine) mgml$^{-1}$ | | | | |
|---|---|---|---|---|---|
| (Ethanol) gl$^{-1}$ | 1.0 | 2.0 | 3.0 | 4.0 | 5.0 |
| 100 | 0.023 | 0.014 | 0.013 | 0.013 | 0.013 |
| 200 | 0.033 | 0.017 | 0.014 | 0.013 | 0.013 |
| 300 | 0.042 | 0.031 | 0.019 | 0.015 | 0.013 |
| 400 | 0.050 | 0.043 | 0.030 | 0.021 | 0.013 |
| 500 | 0.048 | 0.050 | 0.040 | 0.031 | 0.018 |

Reflectance$^{-1}$ of a blank disc (developed with H$_2$O) 0.013
*A reflectance$^{-1}$ value of 0.015 or below indicates no visible colour formation.

TABLE 4

Threshold Test for Alcohol.
Dye: N,N Bis Hydroxyethyl 3-Toluidine

| Alcohol Concentration | Reflectance$^{-1}$* Mediator (Cysteine) mgml$^{-1}$ | | | |
|---|---|---|---|---|
| (Ethanol) gl$^{-1}$ | 1.0 | 2.0 | 4.0 | 5.0 |
| 100 | 0.045 | 0.018 | 0.018 | 0.018 |
| 200 | 0.036 | 0.039 | 0.018 | 0.018 |
| 300 | 0.042 | 0.053 | 0.018 | 0.017 |
| 400 | 0.040 | 0.059 | 0.032 | 0.019 |
| 500 | 0.050 | 0.067 | 0.040 | 0.024 |

Reflectance$^{-1}$ of a blank disc (developed with H$_2$O) 0.016
*A reflectance$^{-1}$ value of 0.019 or below indicates no visible colour formation.

TABLE 5

Threshold Test for Cholesterol
Dye: 3-Hydroxy 2,4,6 Trimbromobenzoic Acid

| Cholesterol Concentration | Reflectance$^{-1}$* Mediator Sodium Mercaptoethane Sulphonate mgml$^{-1}$ | | | | |
|---|---|---|---|---|---|
| mg$^{-1}$ | 2 | 3 | 4 | 6 | 7 |
| 100 | 0.018 | 0.017 | 0.016 | 0.016 | 0.016 |
| 150 | 0.026 | 0.021 | 0.019 | 0.016 | 0.016 |
| 200 | 0.032 | 0.023 | 0.023 | 0.018 | 0.018 |
| 250 | 0.041 | 0.052 | 0.039 | 0.024 | 0.020 |
| 300 | 0.044 | 0.050 | 0.047 | 0.032 | 0.026 |

Reflectance$^{-1}$ of a blank disc 0.016
*A reflectance$^{-1}$ value of 0.020 or below indicates no visible colour formation.

We claim:

1. Colorimetric analytical apparatus comprising a test element including a support, the support carrying a zone including a dried enzyme composition, a predetermined amount of a thiol mediator and a dyestuff, the enzyme composition being arranged to produce hydrogen peroxide upon contact of the zone with an analyte, the dyestuff providing a colorimetric display upon reaction with hydrogen peroxide, said colorimetric display being produced by a reversible covalent condensation reaction in the presence of the mediator, the mediator being adapted until exhausted to scavenge hydrogen peroxide and prevent said colorimetric displays said mediator being selected from the group consisting of sodium mercaptoethane sulphonate and sodium mercaptopropane sulphonate, dithioerythrithol, dithiothreitol, mercapto dextran and glutathione.

2. Apparatus as claimed in claim 1, further comprising a peroxidase adapted to catalyse said display by reaction of the dyestuff and hydrogen peroxide.

3. Apparatus as claimed in claim 1, wherein the mediator is selected from the group consisting of mercaptoalkyl sulphonate salts.

4. Apparatus as claimed in claim 1, further comprising a microporous article covering said zone.

5. Apparatus as claimed in claim 1 wherein the zone is covered by a membrane or reaction pad secured to the support.

6. Apparatus as claimed in claim 4, wherein said display is dependent on the concentration of analyte within a solution applied to the zone.

7. Apparatus as claimed in claim 1 wherein the enzyme composition is alcohol oxidase, derived from Hansenula polymorpha.

8. Apparatus as claimed in claim 1 wherein the analyte is alcohol, cholesterol, lactate, uric acid. glycerol, triglyceride, glutamate, glucose, choline, or NADH.

9. Apparatus as claimed in claim 1 wherein the enzyme composition comprises an enzyme stabilised with a polyelectrolyte and cyclic polyol.

10. A test strip as claimed in claim 1 wherein the zone is elongate and provided at one end with a receptacle for application of the analyte, the colorimetric display being arranged to extend from said one end of the zone, the length of the display from said one end affording an indication of the concentration of analyte in a solution applied to the apparatus.

* * * * *